US012439980B2

(12) United States Patent
Saxton et al.

(10) Patent No.: US 12,439,980 B2
(45) Date of Patent: Oct. 14, 2025

(54) THERAPEUTIC BURP CLOTH

(71) Applicant: Munchkin, Inc., Van Nuys, CA (US)

(72) Inventors: Matthew Joseph Saxton, Moorpark, CA (US); Kaitlyn Giselle Miguel Flores, Cary, NC (US); Laura Ellen Biedebach, Franklin, TN (US)

(73) Assignee: MUNCHKIN, INC., Van Nuys, CA (US)

( * ) Notice: Subject to any disclaimer, the term of this patent is extended or adjusted under 35 U.S.C. 154(b) by 540 days.

(21) Appl. No.: 17/403,311

(22) Filed: Aug. 16, 2021

(65) Prior Publication Data

US 2022/0047003 A1 Feb. 17, 2022

Related U.S. Application Data

(60) Provisional application No. 63/065,794, filed on Aug. 14, 2020.

(51) Int. Cl.

| | |
|---|---|
| ***A41D 1/215*** | (2018.01) |
| ***A41B 13/10*** | (2006.01) |
| ***A61F 7/08*** | (2006.01) |
| ***A61F 7/10*** | (2006.01) |
| *A61F 7/00* | (2006.01) |

(52) U.S. Cl.

CPC ................ *A41D 1/215* (2018.01); *A61F 7/08* (2013.01); *A61F 7/10* (2013.01); *A41B 13/10* (2013.01); *A61F 2007/0019* (2013.01)

(58) Field of Classification Search

CPC ........ A41D 1/215; A43B 13/10; A43B 13/103

See application file for complete search history.

(56) References Cited

U.S. PATENT DOCUMENTS

| | | | | | |
|---|---|---|---|---|---|
| 2,831,193 | A * | 4/1958 | Terry | A41B 13/10 | 2/46 |
| 2,955,293 | A * | 10/1960 | Peterson | A41B 13/10 | 2/48 |
| D350,435 | S * | 9/1994 | Smith, IV | D3/261 | |
| D408,138 | S * | 4/1999 | Mracna | D3/261 | |
| 6,327,712 | B1 * | 12/2001 | Armstrong | A41D 1/215 | 2/104 |
| 7,316,035 | B2 * | 1/2008 | Archambault | A41D 13/04 | 2/48 |
| D585,631 | S * | 2/2009 | Barclay | D2/861 | |
| 9,210,954 | B1 * | 12/2015 | Eischeid | A41B 13/103 | |
| 10,264,831 | B1 * | 4/2019 | Hemker | A61F 5/03 | |
| 11,832,659 | B1 * | 12/2023 | Solotoff | A41B 1/08 | |
| 2009/0024102 | A1 * | 1/2009 | Piret | A61F 13/12 | 604/385.03 |
| 2011/0162125 | A1 * | 7/2011 | Nilforushan | A61F 7/02 | 165/47 |
| 2016/0066629 | A1 * | 3/2016 | Marcum | A41D 13/04 | 2/46 |
| 2016/0287928 | A1 * | 10/2016 | Darnell | A63B 21/4037 | |
| 2018/0027907 | A1 * | 2/2018 | Singer | A61L 9/12 | |
| 2020/0214375 | A1 * | 7/2020 | Insabella-Sabo | A41D 27/12 | |

* cited by examiner

*Primary Examiner* — Katharine G Kane

(74) *Attorney, Agent, or Firm* — ArentFox Schiff LLP; Robert Z. Evora, Esq.

(57) ABSTRACT

A therapeutic burp cloth having at least one panel and at least one pocket. The therapeutic burp cloth is adapted to be worn by a caregiver while holding an infant. The pockets are adapted to receive heat pads, cold pads and therapeutic inserts for comforting the infant and the caregiver during use.

16 Claims, 12 Drawing Sheets

THERAPEUTIC BURP CLOTH

CROSS REFERENCE TO RELATED APPLICATIONS

This Non-Provisional U.S. Application claims priority to U.S. Provisional Patent Application Ser. No. 63/065,794 filed Aug. 14, 2020, the content of which is hereby incorporated by reference herein in its entirety into this disclosure.

TECHNICAL FIELD

The subject disclosure relates generally to a burp cloth and burp cloth system for use with an infant and adult. The burp cloth is adapted for use with hot and cold therapy and may include other therapeutic uses and capabilities for contributing to an infant and adult's well-being.

BACKGROUND

Heat therapy and cold therapy are two techniques common in the physical therapy profession for alleviating pain and symptoms related to numerous injuries and aliments. In the past, parents and caregivers have attempted to adapt hot and cold therapy for use with infants, toddlers and young children. While these treatments generally fall into the category of "home remedies," there are few products specifically adapted for use with infants and small children. Heat therapy may be desirable for use with infants because soothing warmth may help calm babies suffering from colic or upset stomachs. Cold therapy may be desirable because cooling relief may help soothe a child from the discomfort of a fever, inflammation, teething pain or provide relief from bumps and bruises. Additionally, for nursing mothers, heat therapy may be especially advantageous to help alleviate the pain associated with blocked milk ducks. However, infants and small children are quite sensitive to heat and cold, while parents struggle to apply these therapies in an efficacious manner.

Thus, there is a need for a system adapted for heat and cold therapy for use with infants and caregivers that minimizes hassle, potential discomfort, and the difficulties associated with attending to the variety of factors that contribute to an infant's constantly evolving condition, while maximizing the comfort, happiness and homeostasis of both the child and the caregiver.

SUMMARY

The present subject disclosure presents a simplified summary of the subject disclosure in order to provide a basic understanding of some aspects thereof. This summary is not an extensive overview of the various embodiments of the subject disclosure. It is intended to neither identify key or critical elements of the subject disclosure nor delineate any scope thereof. The sole purpose of the subject summary is to present some concepts in a simplified form as a prelude to the more detailed description that is presented hereinafter.

While various aspects, features, or advantages of the subject disclosure are illustrated in reference to burp cloths, such aspects and features also can be exploited in various other childcare systems.

To the accomplishment of the foregoing and related ends, the subject disclosure, then, comprises the features hereinafter fully described. The following description and the annexed drawings set forth in detail certain illustrative aspects of one or more embodiments of the disclosure. However, these aspects are indicative of but a few of the various ways in which the principles of the subject disclosure may be employed. Other aspects, advantages and novel features of the subject disclosure will become apparent from the following detailed description of various example embodiments of the subject disclosure when considered in conjunction with the drawings.

In one exemplary embodiment, the present subject disclosure is a therapeutic burp cloth. The therapeutic burp cloth has a top panel, a middle panel, and a bottom panel. At least one panel contains a pocket therein. The pockets are adapted to receive heat pads, cold pads and therapeutic inserts for comforting an infant and caregiver during use.

In another exemplary embodiment, the present subject disclosure is a therapeutic burp cloth kit. The kit includes a therapeutic burp cloth having at least one panel and at least one pocket. The kit also includes at least one heat pad, at least one cold pad, at least one therapeutic insert and one dispenser.

BRIEF DESCRIPTION OF THE DRAWINGS

Various exemplary embodiments of this disclosure will be described in detail, wherein like reference numerals refer to identical or similar components or steps, with reference to the following figures, wherein.

DETAILED DESCRIPTION

Figure 1:
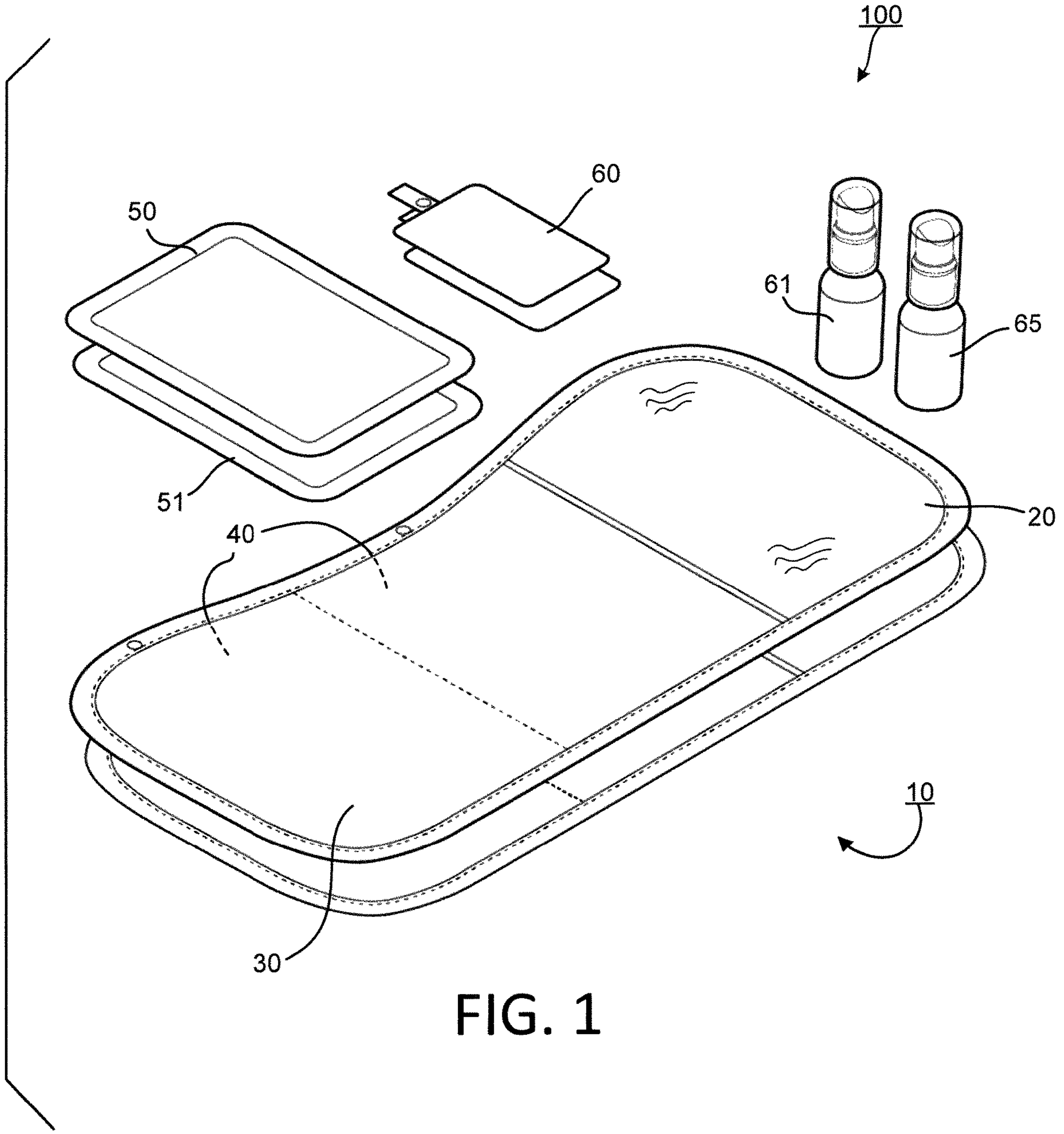
FIG. 1 is a top perspective view of a therapeutic burp cloth and a therapeutic burp cloth kit.

Particular embodiments of a therapeutic burp cloth will now be described in greater detail with reference to the figures.

The subject disclosure is described with reference to the drawings, wherein like reference numerals are used to refer to like elements throughout. In the following description, for purposes of explanation, numerous specific details are set forth in order to provide a thorough understanding of the present disclosure. It may be evident, however, that the present disclosure may be practiced without these specific details.

Figure 4:
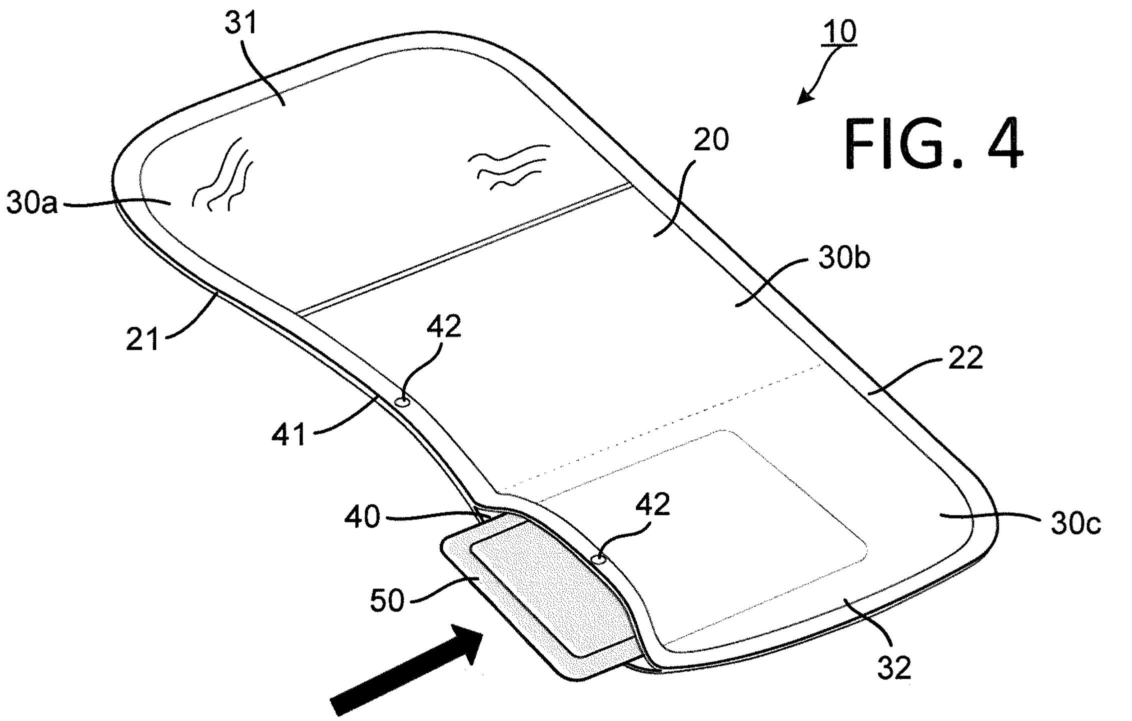
FIG. 4 is a front perspective view of a therapeutic burp cloth with a heat pad installed therein.
Figure 5:
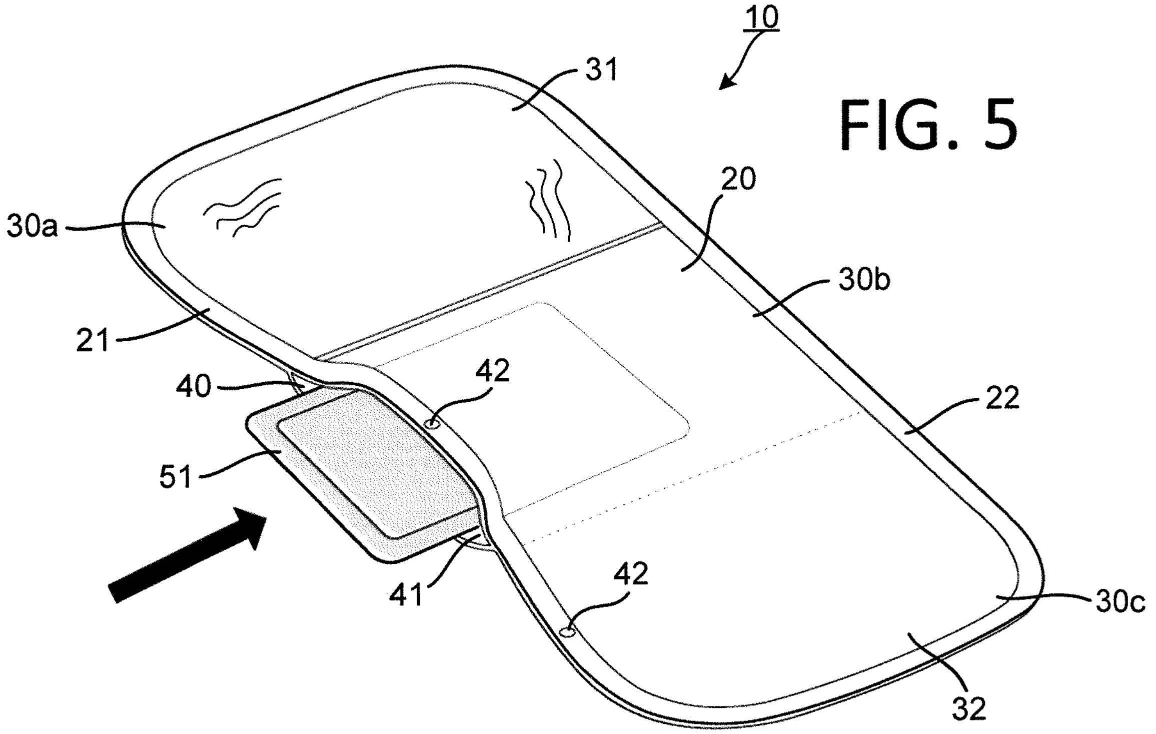
FIG. 5 is a front perspective view of a therapeutic burp cloth with a cold pad installed therein.

FIG. 1 illustrates a therapeutic burp cloth 20 and accompanying accessories that may be embodied as a system 100. Alternatively, the system can be embodied as a kit 10 including therapeutic inserts 60 and aromatic essential oils 61 and dispensers 65. The therapeutic burp cloth 20 may have at least one panel 30 and at least one pocket 40 (FIGS. 4-5). As shown, the therapeutic burp cloth system 10 may include at least one heat pad 50 and/or at least one cold pad 51. The therapeutic burp cloth system 10 may include at least one therapeutic insert 60. The therapeutic insert 60 may be adapted for aromatherapy to enhance the therapeutic effect of the therapeutic burp cloth system 10. Aromatic essential oils 61 may be provided in the therapeutic burp cloth system 10 and may be dispensed by at least one dispenser 65 to provide therapy for an infant and/or a caregiver during use.

Figure 2:
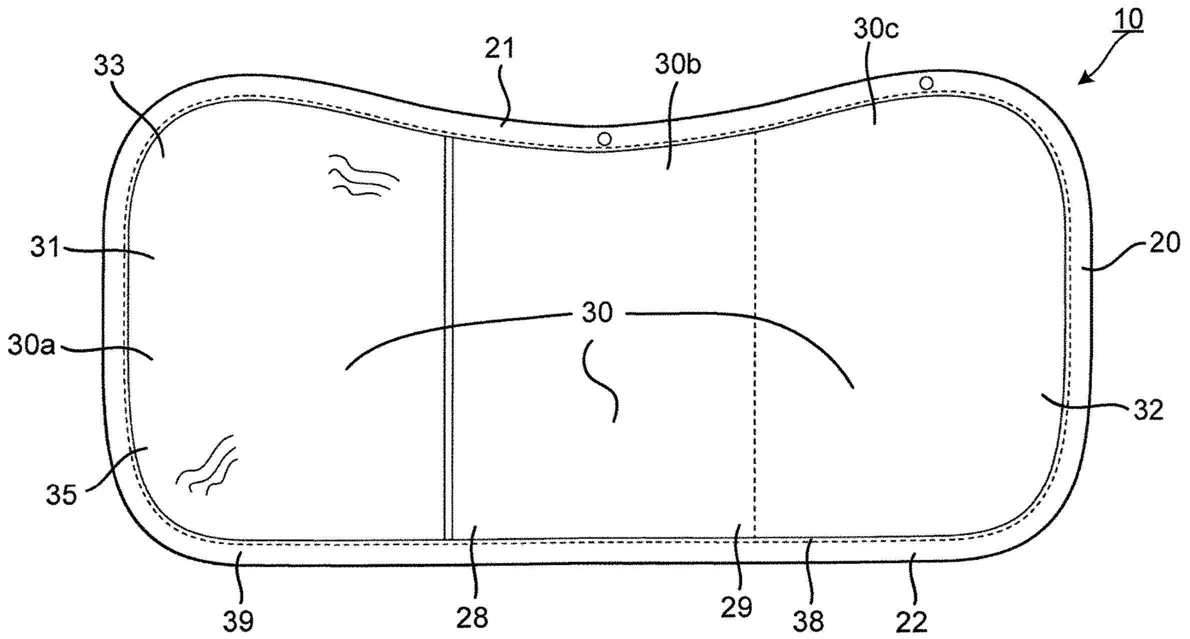
FIG. 2 is a front view of a therapeutic burp cloth-.
Figure 3:
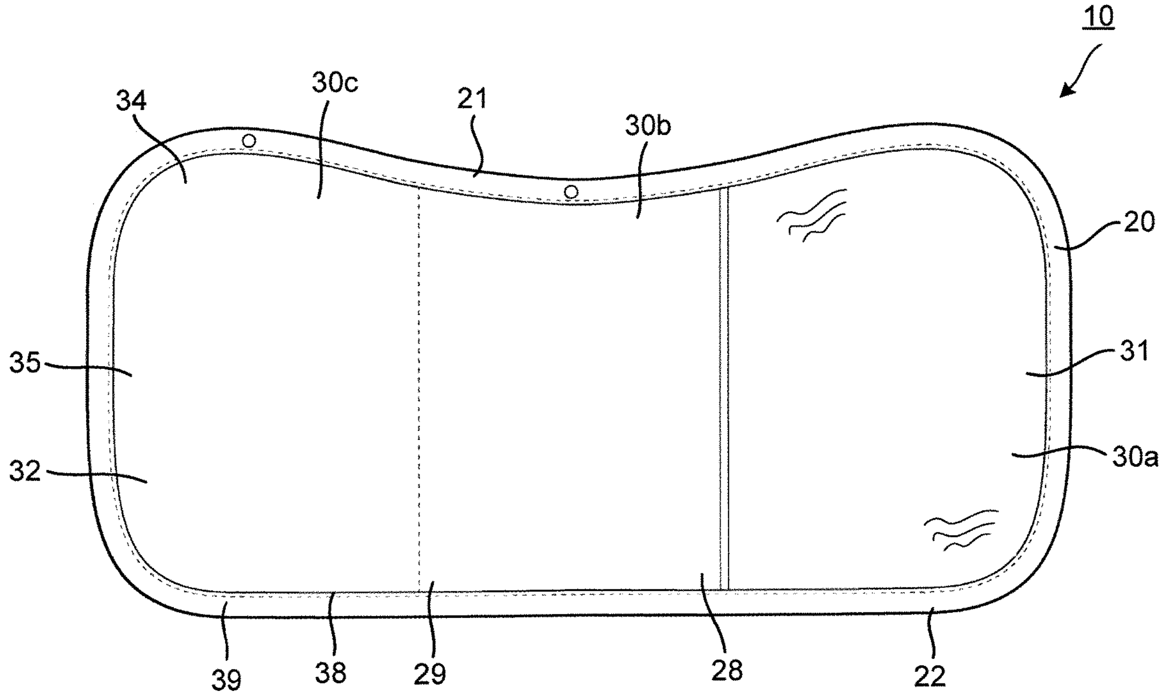
FIG. 3 is a rear view of a therapeutic burp cloth.

FIGS. 2-3 show a front side 33 and a rear side 34 of the therapeutic burp cloth 30, respectively. The therapeutic burp cloth 20 may be formed from several panels 30 (30*a*, 30*b*, 30*c*) that are joined together as a panel assembly. The therapeutic burp cloth 20 may have a top portion 31 and a bottom portion 32. The therapeutic burp cloth 20 may be adapted for use with the top portion 31 resting over a caregiver's shoulder (see FIGS. 11-12). Alternatively, the therapeutic burp cloth 20 may be used with either the top portion 31 or the bottom portion 32 closer to the caregiver's head. A perimeter portion 39 may surround the panels 30. At least one perimeter seam 38 may extend around the perimeter portion 39 and surround the panels 30. The perimeter seam 38 may extend through a thickness of the therapeutic burp cloth 20 from the front side 33 to the rear side 34. The rear side 34 may rest against a caregiver's body and an infant may rest on the front side 33. Alternatively, the therapeutic burp cloth 20 is reversible and may be used with either the front side 33 or rear side 34 in contact with the infant. This allows the caregiver to use the therapeutic burp cloth 20 on either the left or right side of the body. The therapeutic burp cloth 20 may be constructed as a single piece, or individual panels 30 may be joined together through stitching, adhesives or other conventional techniques for attaching fabric and the like.

Figure 11:
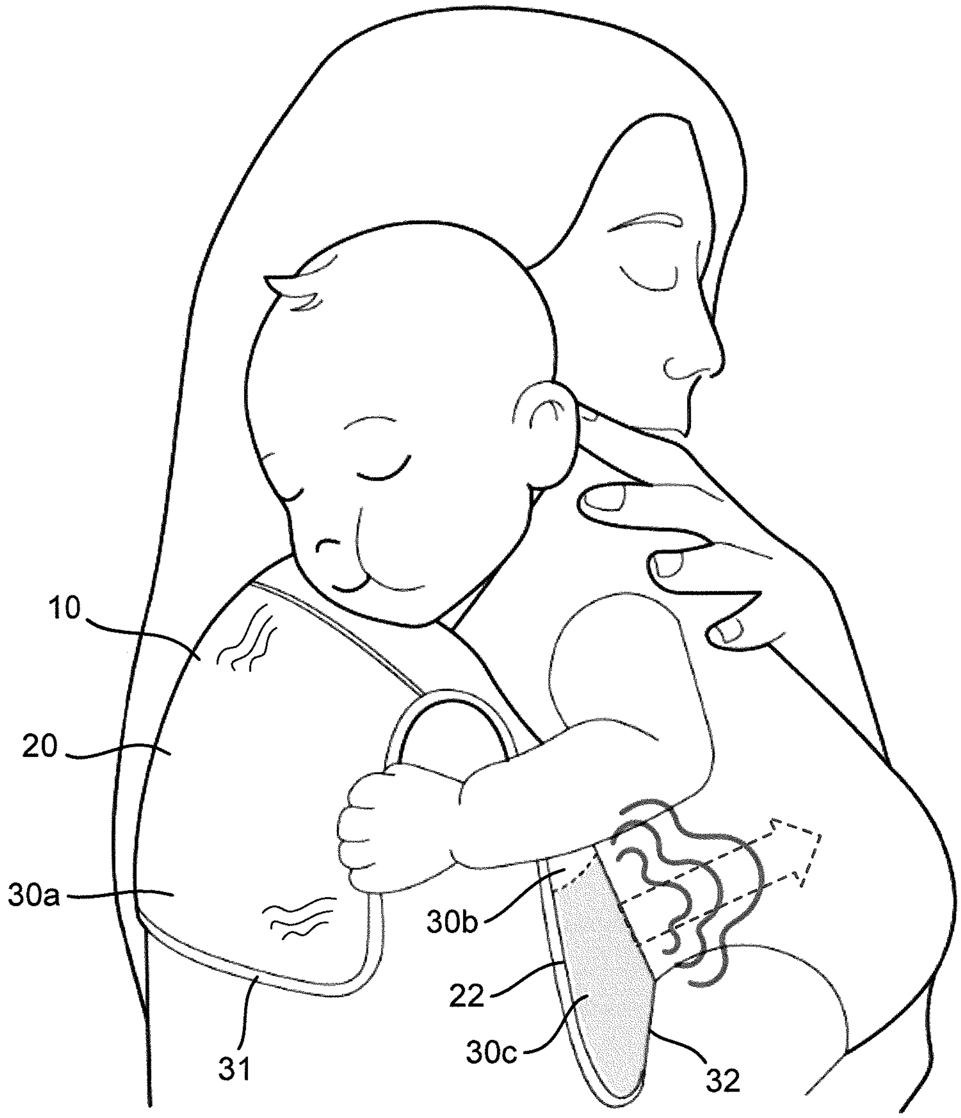
FIG. 11 is a side view of a mother holding an infant with a heat pad installed in a therapeutic burp cloth.

As shown in FIGS. 2-3, the therapeutic burp cloth 20 may be constructed of three panels 30, including a top panel 30*a*, a middle panel 30*b* and a bottom panel 30*c*. The top panel 30*a* may be adapted to hang over the caregiver's shoulder and provide a surface upon which an infant may burp and rest his or her head (FIG. 11). The top panel 30*a* may be attached at an upper portion 28 of the middle panel 30*b*, while the bottom panel 30*c* may be attached at a lower portion 29 of the middle panel 30*b*. The top panel 30*a* and/or either the middle panel 30*b* and/or the bottom panel 30*c*, may be liquid resistant and may be resistant to staining. Alternatively, the panels 30 may be liquid-absorbent. The panels 30 may be easy to wash and clean. The panels 30 may be made of cotton and/or any other suitable textile or material such as neoprene, elastane, polyester, wool, woven synthetic fabrics, natural woven fiber fabrics and the like in order to provide the desired material properties and textures during use. Anti-slip features or textures may be disposed on either side of the therapeutic burp cloth 20 in order to facilitate better grip and stability during use. The panels 30 may be comprised of several different materials concurrently and may be arranged in a layered configuration. The panels 30 may display a design, pattern, brand identifier, image or other indicia that may entertain, inform or please the user.

The middle panel 30*b* and the bottom panel 30*c* may be adapted to have pockets 40 contained therein (FIGS. 4-5). The pockets 40 may be adapted to contain the heat pads 50, the cold pads 51 and/or the therapeutic inserts 60 adapted for use with aromatic essential oils 61 that provide therapeutic effects for both the caregiver and the infant when in use. It is contemplated that additional panels 30 may be formed in the therapeutic burp cloth 20 and that any of the panels 30 may contain pockets 40 therein.

As shown in FIGS. 2-5, the therapeutic burp cloth 20 may be reversible and adapted for use with either a left or a right shoulder. The therapeutic burp cloth 20 may have an inner edge 21 and an outer edge 22. An opening 41 may be disposed along the inner edge 21 for accessing the pocket 40 contained in each respective panel 30. Alternatively, the openings 41 for the pockets 40 may be disposed along the outer edge 22 of the therapeutic burp cloth 20. As shown in FIGS. 2-5, the inner edge 21 contains the openings 41 for the pockets 40. The inner edge 21 is adapted to contour to a caregiver's body and an infant's head and body profile. The inner edge 21 may be curved at both the top portion 31 and the bottom portion 32 of the therapeutic burp cloth 20. The curve of the inner edge 21 may be semi-circular, semi-elliptical, U-shaped, V-shaped, M-shaped, or sinusoidal with a wave pattern of varying amplitude and frequency, and/or substantially any other shape that may perform the function recited in this subject disclosure. The curve of the inner edge 21 may be symmetrical between the top portion 31 and the bottom portion 32, or the curve may be asymmetrical with the top portion 31 or the bottom portion 32 having a greater surface area than the opposite portion. The outer edge 22 may be substantially straight, or it may possess any of the curved features discussed above in reference to the inner edge 21.

While the therapeutic burp cloth 20 may be used with either the inner edge 21 or the outer edge 22 closer to the caregiver's center, the therapeutic burp cloth 20 is adapted for the inner edge 21 to be closest to the caregiver's center when in use and arranged over a caregiver's shoulder (See FIGS. 11-14). The ergonomic design of the therapeutic burp cloth 20 provides ample surface area to protect the caregiver's clothes from any spit-up or discharge from the infant, while also facilitating the comfort of both the infant and the caregiver.

FIG. 1 details some of the related accessories that may be packaged and provided along with the therapeutic burp cloth system 10. In addition to the burp cloth 20, the therapeutic burp cloth system 10 and kit 100 may contain the heat pads 50 and the cold pads 51. The heat pads 50 and the cold pads 51 may be gel packs capable of freezing in a freezer 78 and/or heating in a microwave 77 or in hot water (see FIGS. 16-18). The heat pads 50 and the cold pads 51 may be reusable. Heat pads 50 are desirable for use with infants because soothing warmth may help calm babies suffering from colic or upset stomachs. Cold pads 51 are desirable because cooling relief may help soothe a child from the discomfort of a fever, inflammation, teething pain or provide relief from bumps and bruises.

The therapeutic burp cloth 20 is designed so that the therapeutic effects of the heating and cooling applications may extend to both the infant and the caregiver during use.

The panels 30 are adapted so that the heating and cooling effects radiate through both the front side 33 and the rear side 34 of the therapeutic burp cloth 20. That is, when a caregiver is using the therapeutic burp cloth 20 with the heat pad 50, the soothing warmth may comfort both the infant and the caregiver simultaneously. Similarly, when a caregiver is using the therapeutic burp cloth 20 with the cold pad 51, the cooling effect may provide relief to both the infant and caregiver simultaneously. The panels 30 may include vents that may be resealable, in order to modulate the heating, cooling or aromatic effects.

Additionally, the therapeutic burp cloth 20 may provide different therapeutic effects to the caregiver and the infant simultaneously. For example, the infant may require heat therapy, while the caregiver desires cold therapy. In this situation both the heat pad 50 and the cold pad 51 may be used simultaneously, and the therapeutic insert 60 may be used to limit the desired effects to the specific user by blocking either heat or cold. The therapeutic insert 60 may have hot or cold shielding properties, or the therapeutic burp cloth 20 may include separate temperature shields (not shown).

For nursing mothers, the heat therapy provided by the heat pad 50 may be especially advantageous to help alleviate the pain associated with blocked milk ducks. The heat therapy, cold therapy and aromatherapy provided by the therapeutic burp cloth 20 remains efficacious after the infant has outgrown the nursing stage, and the therapeutic burp cloth 20 is adapted to provide heating and cooling relief to both caregiver and child whenever desired or necessary.

Figure 10:
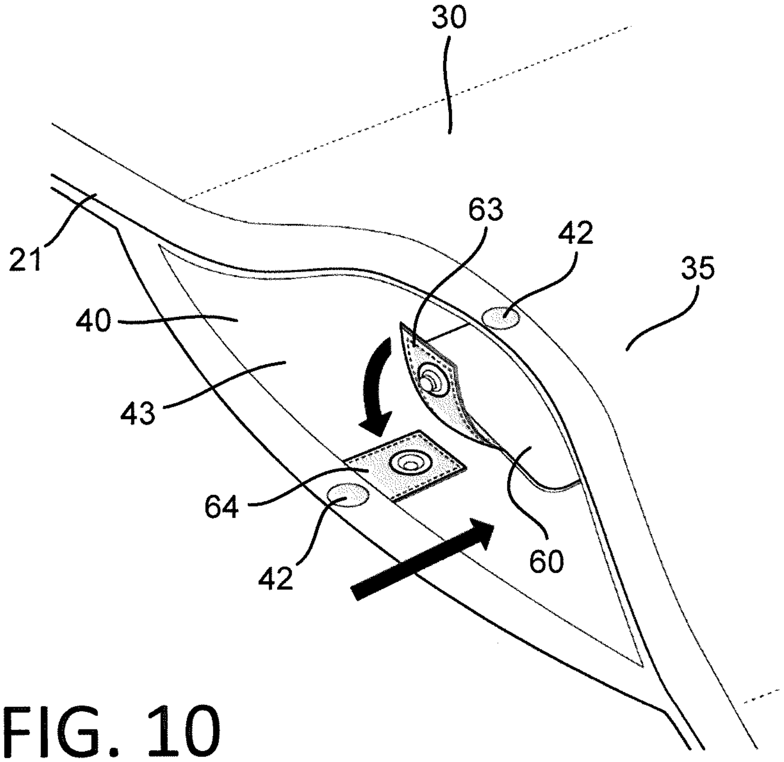
FIG. 10 is a close-up front perspective view of a therapeutic burp cloth with an aromatherapy pad installed therein.

As shown in FIG. 1, the therapeutic burp cloth system 10 or kit 100 may include the therapeutic inserts 60. The therapeutic inserts 60 may be adapted to retain scents and provide aromatherapy to both the infant and the caregiver. The therapeutic inserts 60 may be secured within the pockets 40 (FIG. 10). The therapeutic burp cloth system 10 may also contain at least one dispenser 65 for use with the therapeutic inserts 60. The dispenser 65 may dispense an aromatherapy mixture 62 comprised of essential oils 61, soothing herbs, and/or other contents that may benefit both the caregiver and the infant.

It is contemplated that the therapeutic inserts 60 may be electrode pads for use with a conventional TENS Unit and/or EMS Combination Muscle stimulator (not shown) that may be included with the therapeutic burp cloth system 10. The muscle stimulator may provide relaxation, reflexology and acupressure to the caregiver or infant while the therapeutic burp cloth 20 is in use. The therapeutic inserts 60, or the outer surface of the panels 30 may also have a topography that facilitates acupressure for the caregiver and/or infant. The topography may include protrusions, ridges, undulations, textures and the like for facilitating relaxation, acupressure and massage for the infant and/or the caregiver.

Figure 15:
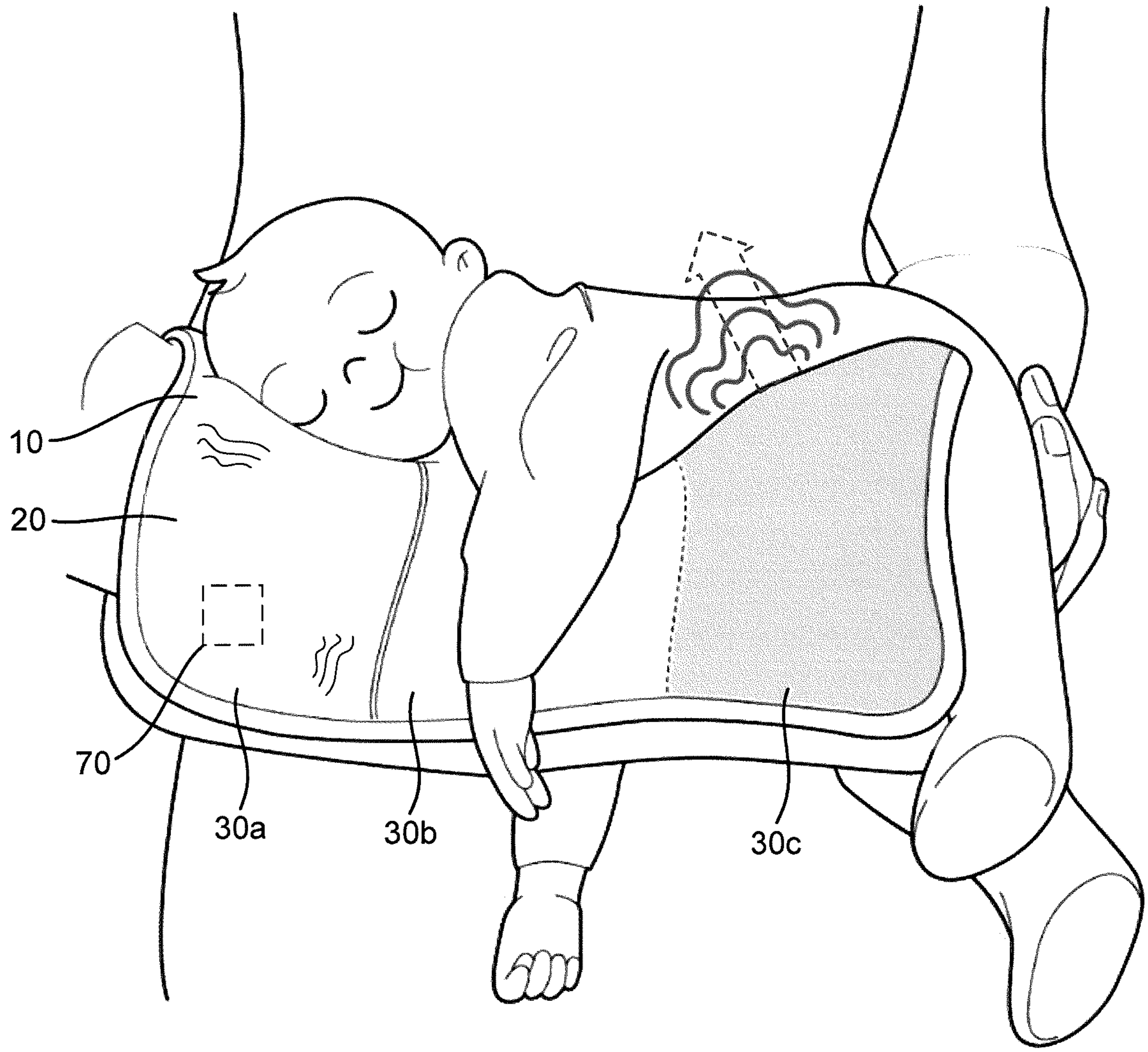
FIG. 15 is a front view of a mother comforting an infant in a horizontal use position with a heat pad installed in a therapeutic burp cloth.
Figure 19:
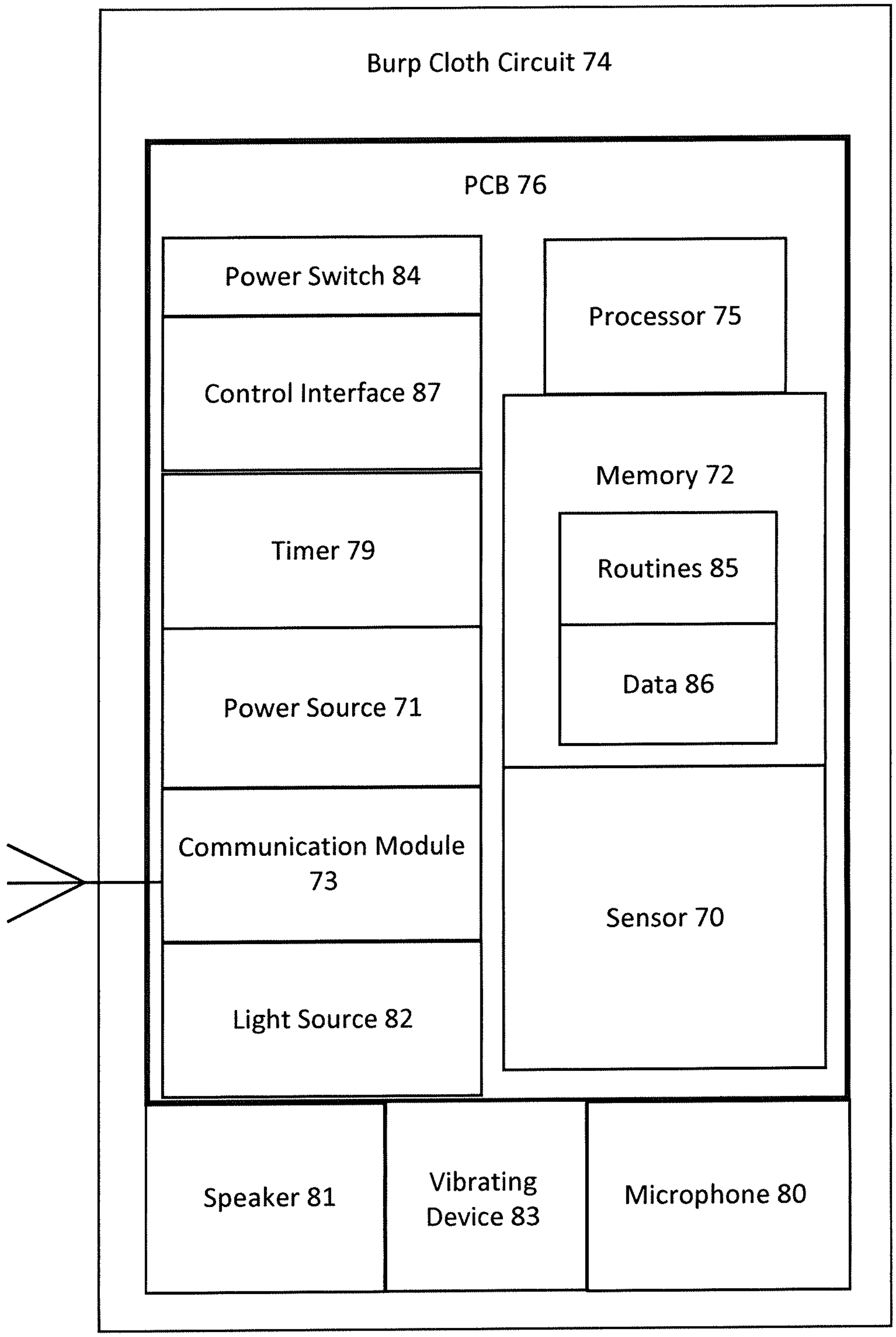
FIG. 19 is a schematic view of a therapeutic burp cloth circuit, according to an exemplary embodiment of the present subject disclosure.

The therapeutic burp cloth 20 may include at least one sensor 70 connected within a burp cloth circuit 74 (see FIGS. 15 and 19). The sensor 70 may be a humidity sensor, a temperature sensor, an acoustic sensor, a sound sensor, a video sensor, a vibration sensor, a chemical sensor, an electric current sensor, an electric potential sensor, a magnetic sensor, a radio sensor, a radiation sensor, a navigational sensor, a position sensor, an angle sensor, a displacement sensor, a distance sensor, a speed sensor, an acceleration sensor, an optical sensor, a light sensor, an imaging sensor, a photon sensor, a pressure sensor, a force sensor, a density sensor, a level sensor, a thermal sensor, a heat sensor, a proximity sensor, a presence sensor, a sonar sensor, a micro-electrical mechanical system sensor, a radar sensor, an ultrasonic sensor, an air pollution sensor, an air quality sensor, a carbon monoxide sensor, a biometric sensor and/or any combination of the above listed sensors.

The sensor 70 may be adapted to measure an infant's body temperature, heart rate, blood pressure, breathing, sleep and/or other biological function. The sensor 70 may record or transmit sound generated by the infant in order to analyze and interpret the physical, mental condition of the infant. The sensor 70 may include a power source 71 and a source of digital memory 72. The sensor 70 may include a communication module 73 that may include a transmitter, a transducer, a transceiver, an antenna, and may be adapted for communication using any of a variety of wireless protocols, such as: IEEE 802.15.4, Wi-Fi, ZigBee, 6LoWPAN, Thread, Z-Wave, radio, Bluetooth Smart, WirelessHART, MiWi and/or including any other communication protocols.

The therapeutic burp cloth 20 may include a burp cloth circuit 74 having a control interface 87, a processor 75, a controller, an integrated CPU, a printed circuit board 76, at least one USB port, the power source 71, a timer 79 and the memory 72 for storing programs, routines 85 and data 86. The burp cloth circuit 74 may include a microphone 80, a speaker 81, a light source 82 that may be a light-emitting diode (LED) light, a vibrating device 83, such as an eccentric motor or actuator, and at least one power switch 84. The sensor 70 may relay data 86 to a controller, smart speaker, cloud server or application on a personal computing device. The controller or personal computing device may contain software or may be part of a cloud computing network for analyzing the data 86 acquired by the sensor 70 and providing instruction or analysis that may assist a caregiver in providing for the infant's well-being.

The therapeutic burp cloth 20 may be adapted to produce a soothing sound through the speaker 81 and/or a vibration caused by the vibrating device 83. The soothing sound may be white noise, static, pink noise, balanced tones, even tones, relaxing tones, sleep tones, customized recordings, custom playlists or streams from apps such as Spotify, Amazon music, and Apple music, podcasts, stories, and/or sing song scripts. The light source 82 may be a LED light or a light bulb and may be adapted for bright light therapy and/or calming light therapy.

The therapeutic burp cloth 20 may be adapted to be left with an infant in a crib, carseat, bouncer or rocker, and the like. The therapeutic burp cloth 20 may be adapted for use with a monitor application (app) for smart devices. A user may input commands into the monitor app that will then be received by the therapeutic burp cloth 20. The monitor app may receive updates, alerts and information transmitted from the therapeutic burp cloth 20, a remote server, a cloud computing network, another client or endpoint device and/or any other communication architecture. The monitor app may communicate directly with the therapeutic burp cloth 20 and/or the sensors 70, and/or may communicate with the therapeutic burp cloth 20 through a network and/or cloud server.

FIGS. 4-5 illustrate the installation and placement of the heat pads 50 and/or the cold pads 51 within the therapeutic burp cloth 20. As shown in FIGS. 4-5, the middle panel 30*b* and the bottom panel 30*c* are disposed with pockets 40 therein. The pockets 40 may include a closing mechanism 42 (see also FIGS. 6-7) that securely closes the pockets 40 and assists in securing the heat pad 50 and/or the cold pad 51 therein. As shown in FIGS. 4-7, the closing mechanism 42 is a snap fastener. However, any conventional fastener may be utilized in the therapeutic burp cloth 20, such as a zipper, hook and loop fastener, magnetic closure, friction closure, and the like, without departing from departing from the broader aspects of the present subject disclosure.

It is contemplated that the bottom panel 30*c* is particularly well adapted for use with the heat pad 50 because when worn over a caregiver's shoulder the bottom panel 30*c* is near to the infant's stomach. The middle panel 30*b* may be well adapted for use with the cold pad 51, as the middle panel 30*b* is near to the infant's upper torso, neck and head when the therapeutic burp cloth 20 is worn over the caregiver's shoulder. However, both the middle panel 30*b* and the bottom panel 30*c* may be used effectively with either the heat pad 50 or the cold pad 51 depending on the user's preference and individual needs.

Figure 6:
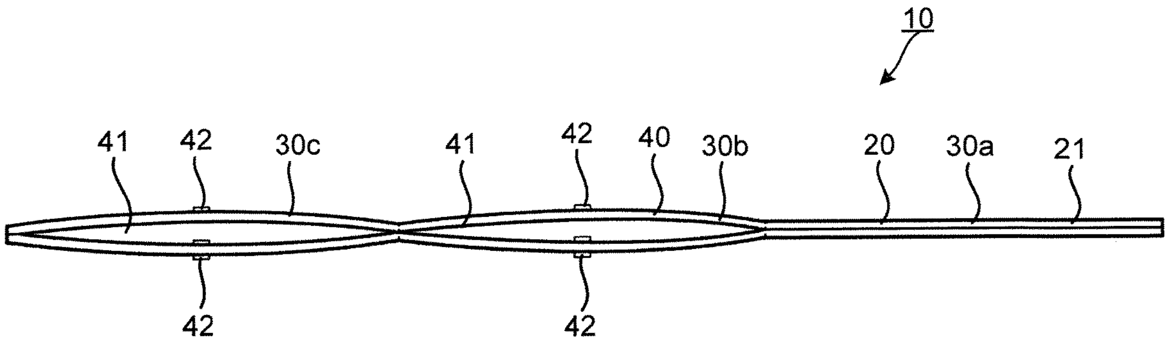
FIG. 6 is a top view of a therapeutic burp cloth.
Figure 7:
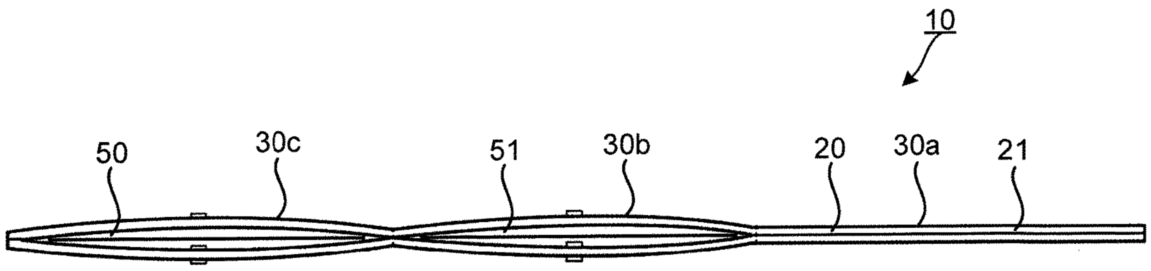
FIG. 7 is a top view of a therapeutic burp cloth with hot and cold pads installed therein.
Figure 8:
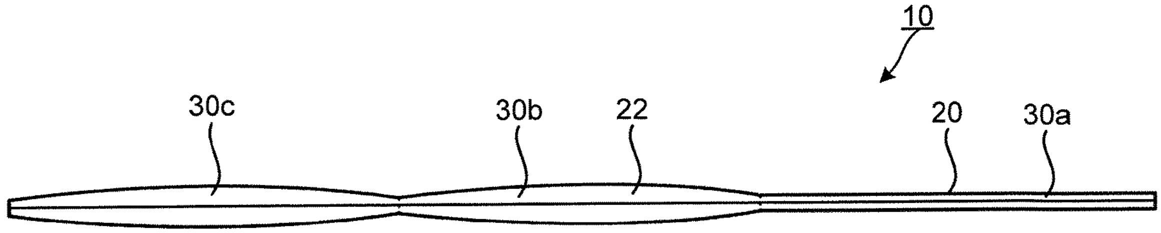
FIG. 8 is bottom view of a therapeutic burp cloth.

FIG. 6 is a top view of the therapeutic burp cloth 20 without the heat pad 50 or cold pad 51 contained therein. This view shows the closing mechanism 42, as shown as a snap fastener, that closes the pockets 40 of the middle panel 30*b* and the bottom panel 30*c*. FIG. 7 is a top view of the therapeutic burp cloth 20 with both the heat pad 50 and the cold pad 51 installed therein. FIG. 8 is a bottom view of the therapeutic burp cloth 20.

The therapeutic burp cloth 20 is designed with the comfort and safety of both the infant and the caregiver in mind. Infants in particular have sensitive skin that may be adversely affected by direct exposure to heat, cold or various essential oils, soothing compounds or mixtures that may be applied on the therapeutic inserts 60. Because the heat pads 50, the cold pads 51 and the therapeutic inserts 60 are installed inside the pockets 40 during use, the infant and caregiver are not directly exposed to these items. Temperatures, both hot and cold, never reach uncomfortable levels for the infant or caregiver because of this configuration. Furthermore, the effect of the therapeutic inserts 60 may be modulated in a positive way by adjusting the material properties and composition of the panels 30 and the pockets 40. In the context of aromatherapy, for example, the scent released by the therapeutic inserts 60 may be gentle and soothing and not overpowering. A light scent may diffuse out of the pocket 40 in a manner that is pleasant and relaxing for both the infant and the caregiver. The material of the panels 30 may be thicker or thinner, or more or less porous in order to control the release of any vapors, scents or palliative and/or medical contents generated or delivered by the therapeutic inserts 60.

Figure 9:
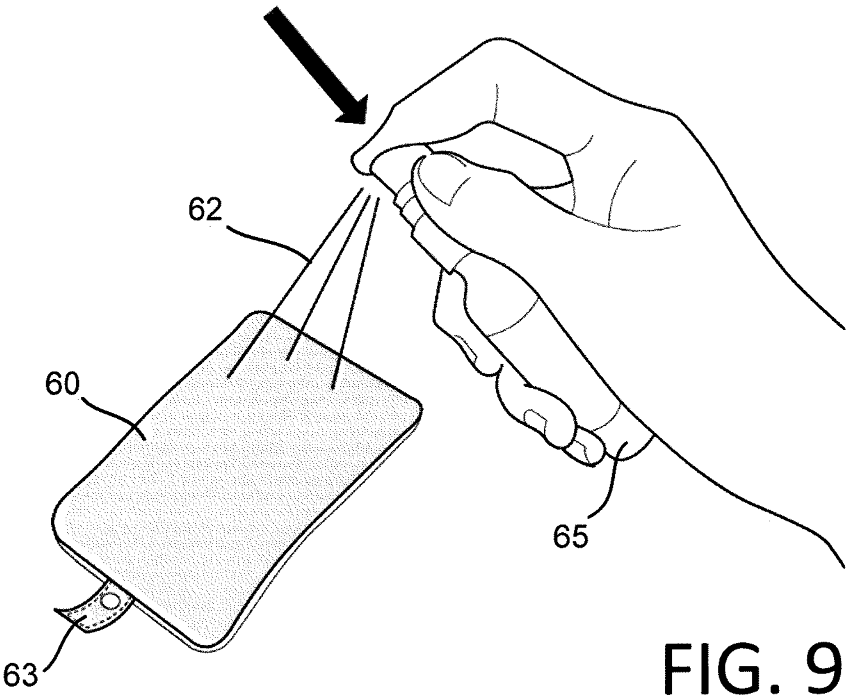
FIG. 9 is front perspective view of an aromatherapy pad in use.

FIGS. 9-10 provide further detail regarding the therapeutic inserts 60 and their installation in the therapeutic burp cloth 20. FIG. 9 shows a caregiver preparing a therapeutic insert 60 by applying a soothing aromatherapy mixture 62 from the dispenser 65 directly on the therapeutic insert 60. As shown in FIGS. 1 and 9, the dispenser 65 may be a spray bottle, but other suitable dispensers may be used or included in the therapeutic burp cloth system 10 or kit 100. The therapeutic inserts 60 may also be pre-treated with appropriate compounds for immediate use. The therapeutic inserts 60 may be disposable or replaceable. The therapeutic inserts 60 may be washable and may be adapted for heating and cooling applications. The therapeutic inserts 60 may be conductive to an electrical current. The therapeutic inserts 60 may also be adapted to shield either heat or cold from the caregiver or infant during use.

FIG. 10 provides further details regarding the installation of the therapeutic insert 60 within the pocket 40 contained in the respective panel 30 of the infant burp cloth 20. The therapeutic insert 60 fits comfortable and securely within the pocket 40 and may be used simultaneously with either the heat pad 50 or the cold pad 51 also installed therein. The therapeutic insert 60 is secured by an attachment mechanism

64 disposed on an interior surface 43 of the pocket 40. Alternatively, the attachment mechanism 64 may be disposed on the exterior surface 35 of the panels 30, or along the inner edge 21 or the outer edge 22 of the therapeutic burp cloth 20. The attachment mechanism 64 and the closing mechanism 42 of the pockets 40 may be adapted as a single mechanism that serves both purposes simultaneously.

As shown in FIG. 10, the attachment mechanism 64 is a snap fastener disposed on the interior surface 43 of the pocket 40 that mates with a complementary attachment tab 63 disposed on the therapeutic insert 60. However, any conventional attachment mechanism 64 may be used to secure the therapeutic insert 60 within the therapeutic burp cloth 20 such as a zipper, hook and loop, hook fastener, carabiner, magnetic attachment, and the like without departing from the broader aspects of the present subject disclosure. Once the therapeutic insert 60 is installed and secured within the pocket 40, the pocket 40 may be closed or sealed. The effects of the therapeutic insert 60 may then extend to the infant and/or the caregiver. If, for example, the therapeutic insert 60 is being used for aromatherapy, a light and pleasant scent may diffuse out of the pocket 40 relaxing both the infant and caregiver.

Figure 12:
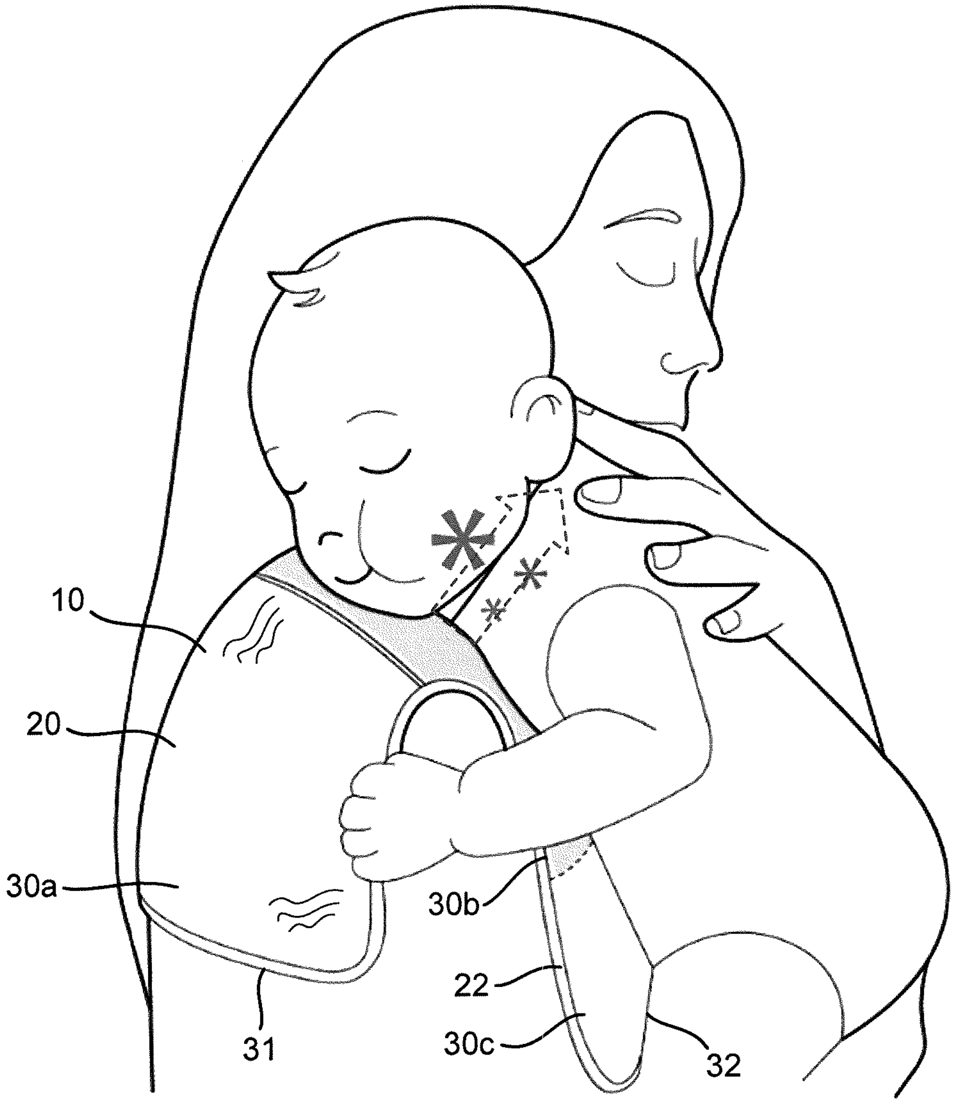
FIG. 12 is a side view of a mother holding an infant with a cold pad installed in a therapeutic burp cloth.
Figure 13:
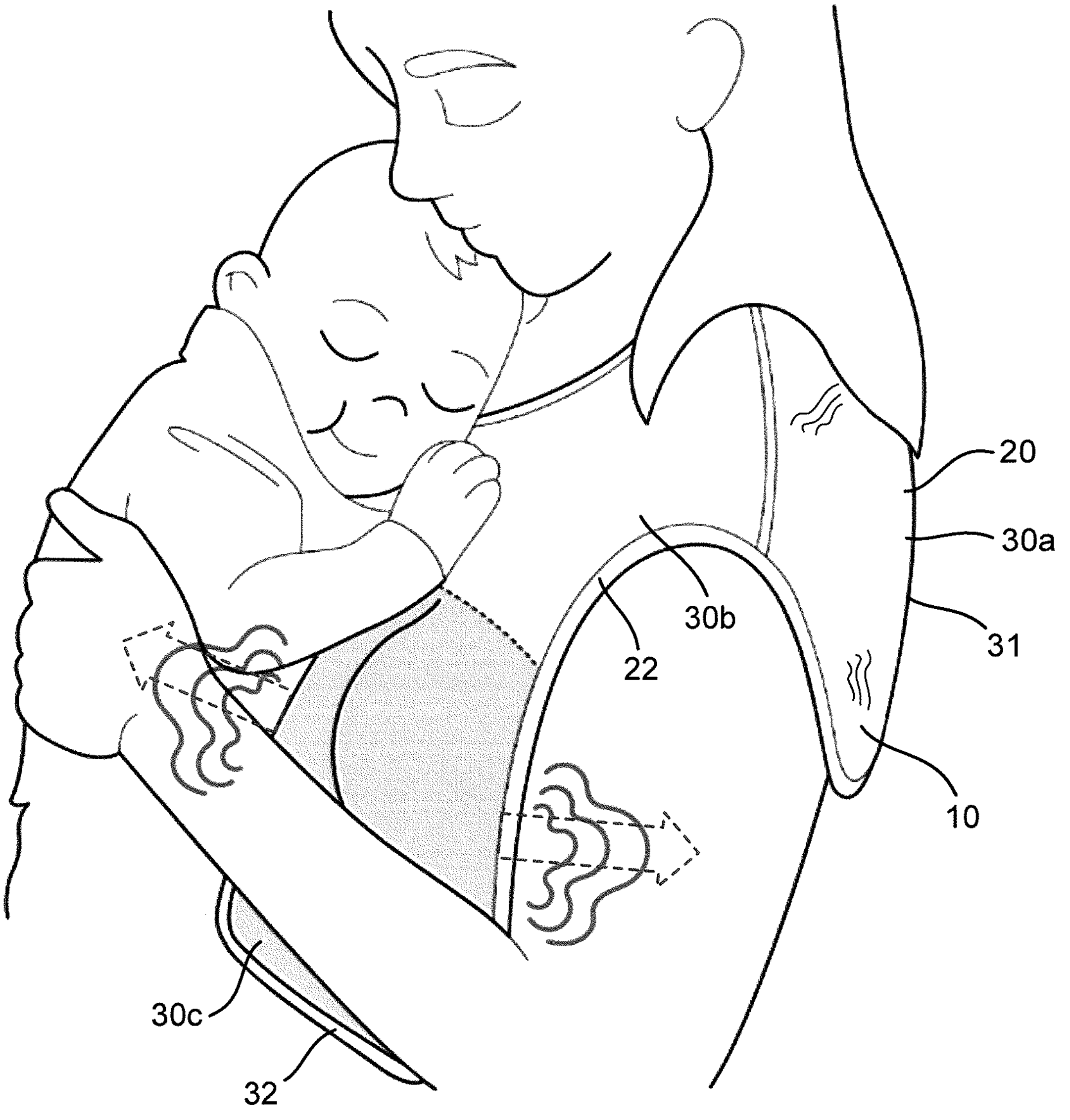
FIG. 13 is a side view of a mother holding an infant with a heat pad installed in a therapeutic burp cloth.
Figure 14:
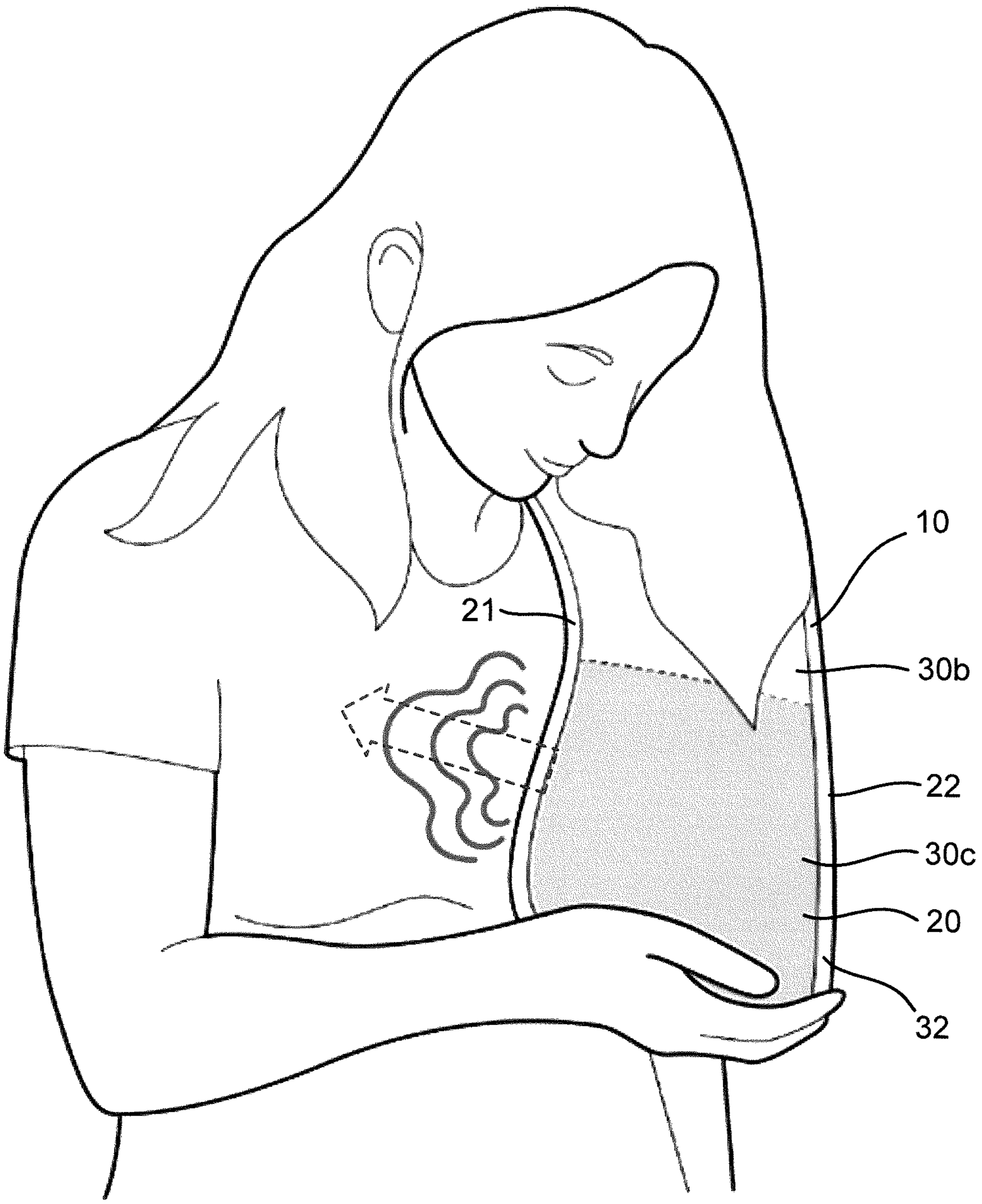
FIG. 14 is a front view of a mother using a therapeutic burp cloth with a heat pad installed therein.

FIGS. 11-13 and 15 illustrate the therapeutic burp cloth 20 in use by a mother and child, while FIG. 14 illustrates the mother using the therapeutic burp cloth 20 independently without the child. The therapeutic burp cloth 20 may be used in numerous use positions. As shown in FIG. 11-12, the therapeutic burp cloth 20 is slung over a single shoulder. The top panel 30*a* hangs over the rear shoulder blade providing coverage for the caregiver and her/his clothing. The middle panel 30*b* rests on the caregiver's chest such that the pocket 40 in the middle panel 30*b*, and by extension the heat pad 50 or the cold pad 51 installed therein, is roughly at the level of the infant's upper torso and head while the infant rests against the caregiver. As shown, the bottom panel 30*c* is at the level of the infant's stomach and lower torso in this same use position. The therapeutic burp cloth 20 may also be used diagonally across the caregiver's chest to comfort an infant in a horizontal or cross-body resting position.

The therapeutic burp cloth 20 may have at least one attachment strap (not shown) to help secure it across a caregiver's chest, around the torso or neck and/or underneath an arm. The at least one attachment strap may assist in securing the therapeutic burp cloth 20 to the infant. The attachment strap may be a leash attached at the top portion 31 of the therapeutic burp cloth 20 that has a fastener disposed at a distal end of the leash and is adapted to mate with a connection disposed on the bottom portion 32 of the therapeutic burp cloth 20. Additional straps may be disposed on either the front side 33 or the rear side 34 that connect the inner edge 21 to the outer edge 22 in order to secure the therapeutic burp cloth 20 to an arm, leg or other appropriate surface. The therapeutic burp cloth 20 may contain at least one flap (not shown) in order to assist in securing the therapeutic burp cloth 20 to the infant. The therapeutic burp cloth 20 may be adapted as an infant garment and may be worn by the child as a shirt, pants, pajamas, onesie, and the like. The therapeutic burp cloth 20 may be adapted for use with existing infant garments, or specialized garments, in order to assist in securing the therapeutic burp cloth 20 to the infant without the active assistance of the caregiver.

FIG. 13 shows the therapeutic burp cloth 20 slung over the mother's shoulder while she is holding the infant. The heat pad 50 is installed in the bottom panel 30*c* of the therapeutic burp cloth 20. The soothing warmth generated by the heat pad 50 is enjoyed by the infant and mother simultaneously.

FIG. 14 shows the mother using the therapeutic burp cloth 20 without the infant. The therapeutic burp cloth 20 may provide heat and cold therapy to the caregiver independently, that is when the caregiver is not holding the infant. For nursing mothers, the heat therapy provided by the heat pad 50 may be especially advantageous to help alleviate the pain associated with blocked milk ducks.

FIG. 15 shows the therapeutic burp cloth 20 in a horizontal use position. As shown in FIG. 15, the infant is resting on the therapeutic burp cloth 20 and cradled in her mother's arms. The infant's head rests on the top panel 30*a*, while the infant's chest rests on the middle panel 30*b* and the infant's stomach rests upon the bottom panel 30*c*. The heat pad 50 is installed in the bottom panel 30*c* and is radiating warm, relaxing heat to the infant's stomach. The infant is fast asleep, and the soothing heat also helps to make the mother calm and serene.

Figure 16:
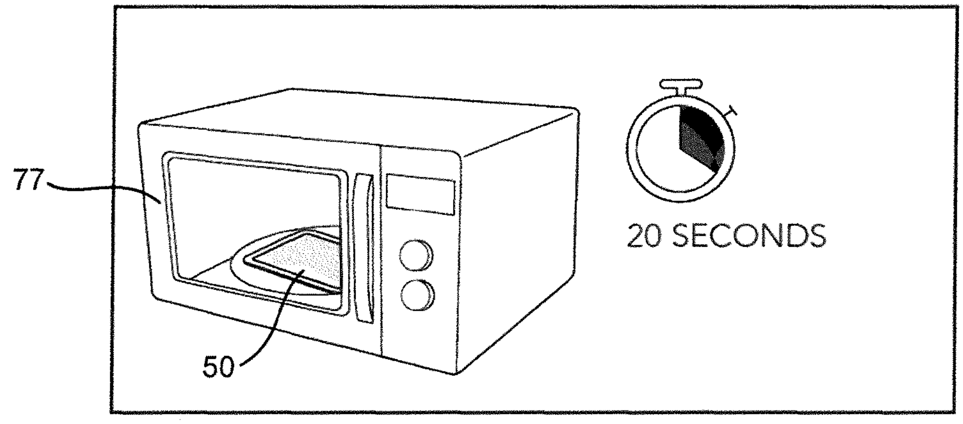
FIG. 16 is a front perspective view of a heat pad being heated in a conventional microwave.
Figure 17:
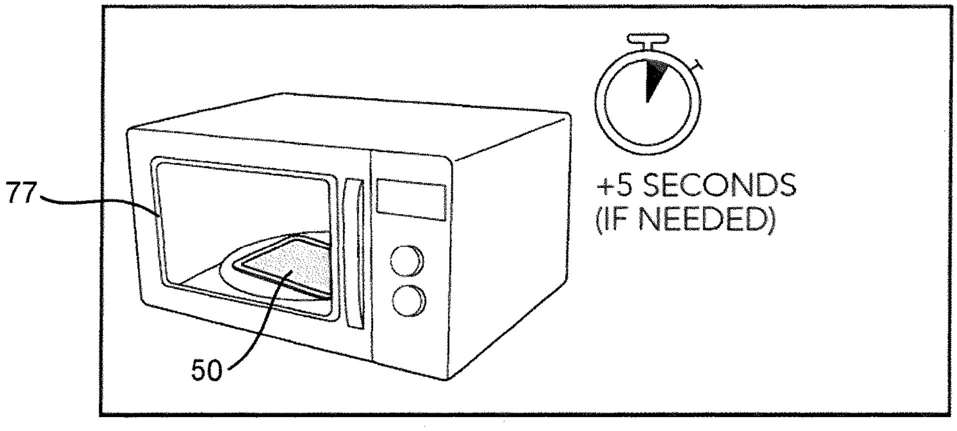
FIG. 17 is a front perspective view of a heat pad being heated in a conventional microwave.

The subject disclosure provides for a method of using the therapeutic burp cloth system 10 or kit 100. A first step in the method may be initially providing a therapeutic burp cloth 20 having at least one pocket 40. A second step may be heating the heat pad 50 for a desired length of time on a stove or in the microwave 77. As shown in FIGS. 16-17, the heat pad 50, in this example, a gel pad, is heated in the microwave 77 for 20 seconds. The heat pad 50 may be heated for as little as 5 seconds or up to 90 seconds depending on the composition and properties of the heat pad 50 used and the desired temperature, the characteristics of the microwave 77 and/or the power level of the microwave setting. On the stove, the heat pad 50 may be inserted into boiling water, or near boiling water for a set time long enough to bring the heat pad 50 to the desired temperature. This may require as little as 10 seconds or up to as long as 5 minutes depending on the temperature of the water and the properties of the heat pad 50 used. The heat pad 50 may be heated by other means, including, but not limited to, chemical reaction, electric charge, fireplace, conventional stove or oven, and the like according to this subject disclosure.

FIG. 17, shows the additional step of heating the heat pad 50 a second time to reach the desired therapeutic temperature. The duration of this additional heating step depends upon the initial temperature obtained during the first heating step, and may take anywhere from a few seconds to a predetermined period of time, e.g., 3 seconds to 3 minutes depending upon the method of heating and specific characteristics of the heat pad 50 and the heating source. The sensor 70 may be a temperature indicator that detects and indicates the temperature of the heat pad 50 specifically or indicates when the heat pad 50 has reached a therapeutic temperature range. The sensor 70 may additionally warn a user when the heat pad 50 is too hot for use.

Figure 18:
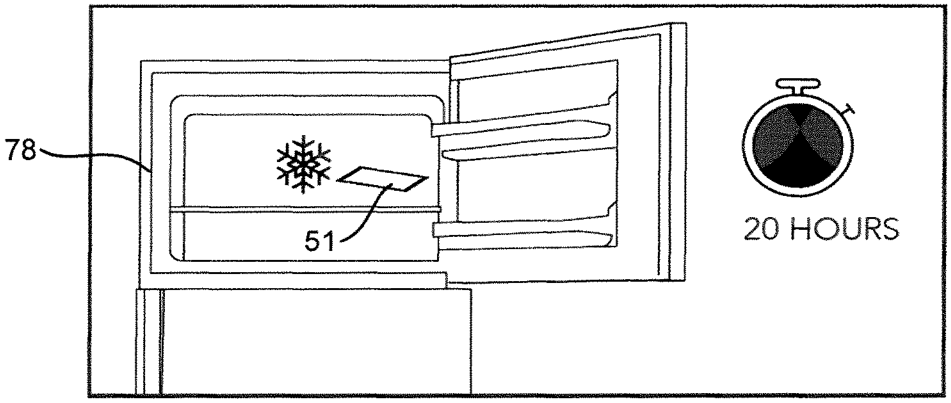
FIG. 18 is a front perspective view of a cold pad being cooled in a conventional freezer.

FIG. 18 shows the additional and/or alternative step of providing a cold pad 51 and the cooling the cold pad 51, in this example a gel pad, to the desired temperature. The cold pad 51 may be cooled in a freezer 78 or a refrigerator for a duration long enough to cool the cold pad 51 to a desired temperature. As shown in FIG. 18, the cold pad 51 may be cooled for a predetermined period of time, e.g., 20 hours in the freezer before use. This amount of time may vary, e.g., between 15 minutes and 24 hours depending on the material characteristics of the cold pad 51, a desired temperature and cold source being used.

Further steps in the method may include inserting the heat pad 50 or the cold pad 51 in the pocket 40 disposed in the therapeutic burp cloth 20 and then positioning the therapeutic burp cloth 20 over a shoulder and resting the infant on the therapeutic burp cloth 20 so that the infant receives either heat or cold therapy on a desired area of the body. Simultaneous steps may include applying aromatic essential oils 61 or the aromatherapy mixtures 62 to the therapeutic insert 60 and then securing the therapeutic insert 60 in the pocket 40 to deliver aromatherapy. A further step in the method may include arranging or positioning the therapeutic burp cloth 20 so that the heat pad 50 or the cold pad 51 simultaneously provides therapy to the caregiver and the infant. The method may also further include the steps of using the sensor 70 disposed in the therapeutic burp cloth 20 to gather biometric data 86, relaying that information by a transceiver (wired or wireless) to a controller or monitoring application for processing and generating reports and/or advice on the infant's heath and biological processes for use by a caregiver to provide the infant care.

As employed in this specification and annexed drawings, the term "or" is intended to mean an inclusive "or" rather than an exclusive "or." Moreover, articles "a" and "an" as used in the subject specification and annexed drawings should generally be construed to mean "one or more" unless specified otherwise or clear from context to be directed to a singular form.

What has been described above includes examples that provide advantages of the subject disclosure. It is, of course, not possible to describe every conceivable combination of components or methodologies for purposes of describing the subject disclosure, but one of ordinary skill in the art may recognize that many further combinations and permutations of the claimed subject matter are possible. Furthermore, to the extent that the terms "includes," "has," "possesses," and the like are used in the detailed description, claims and drawings such terms are intended to be inclusive in a manner similar to the term "comprising" as "comprising" is interpreted when employed as a transitional word in a claim.

The illustrations and examples provided herein are for explanatory purposes and are not intended to limit the scope of the appended claims. It will be recognized by those skilled in the art that changes or modifications may be made to the above described embodiment without departing from the broad inventive concepts of the invention. It is understood therefore that the invention is not limited to the particular embodiments described herein, but is intended to cover all modifications and changes within the scope and spirit of the invention.

What is claimed:

1. A therapeutic burp cloth comprising:

a top panel;

a middle panel; and a bottom panel, wherein the top panel, the middle panel and the bottom panel together form a panel assembly that has an outer perimeter with a first elongated straight edge and a second elongated curved edge, both the first elongated straight edge and the second elongated curved edge extend along the top panel, middle panel and bottom panel, wherein the second elongated curved edge is adapted to contour to a neck of a caregiver;

wherein the top panel attaches to an upper portion of the middle panel and the bottom panel attaches to a lower portion of the middle panel and at least one panel contains a fixed pocket with an opening having a first opening length therein, wherein the opening of the fixed pocket is disposed within the second elongated curved edge of the panel assembly, wherein the fixed pocket has a closing mechanism that seals the fixed pocket in a closed position, wherein at least one pad has a length sized slightly smaller than the first opening length of the fixed pocket so that when the pad is inserted into the fixed pocket and the closing mechanism is in the closed position, the pad is unable to substantially move or exit from within the fixed pocket, and wherein the therapeutic burp cloth is configured to provide therapeutic temperature to an infant and the caregiver simultaneously.

2. The therapeutic burp cloth recited in claim 1, wherein the middle panel and the bottom panel both contain fixed pockets therein.

3. The therapeutic burp cloth recited in claim 1, wherein the at least one pad is a heating pad adapted to be secured in the fixed pocket.

4. The therapeutic burp cloth recited in claim 1, wherein the at least one pad is a cold pad adapted to be secured in the fixed pocket.

5. The therapeutic burp cloth recited in claim 1, further comprising at least one therapeutic insert adapted for aromatherapy.

6. The therapeutic burp cloth recited in claim 5, further comprising an attachment mechanism for securing the therapeutic insert in the fixed pocket.

7. The therapeutic burp cloth recited in claim 6, further comprising an attachment tab disposed on the therapeutic insert that matingly connects with the attachment mechanism.

8. A therapeutic burp cloth comprising:

a panel assembly comprising:

a top panel;

a middle panel; and a bottom panel, wherein the panel assembly has an outer perimeter with a first elongated straight edge and a second elongated curved edge, both the first elongated straight edge and the second elongated curved edge extend along the top panel, middle panel and bottom panel, wherein the second elongated curved edge is adapted to contour to a neck of a caregiver;

a fixed first pocket disposed in the middle panel; and a fixed second pocket disposed in the bottom panel;

wherein a first opening length of the fixed first pocket and a second opening length of the fixed second pocket are disposed within the second elongated curved edge of the panel assembly, wherein a closing mechanism is provided on at least one of the fixed first pocket or the fixed second pocket to seal the pocket in a closed position, and wherein at least one pad has a length sized slightly smaller than at least one of the first opening length or the second opening length so that when the pad is inserted therein and closing mechanism is in the closed position, the pad is unable to substantially move or exit from the pocket; and wherein the therapeutic burp cloth is configured to provided therapeutic temperature to an infant and the caregiver simultaneously.

9. The therapeutic burp cloth recited in claim 8, wherein the second elongated curved edge is a curved inner edge.

10. The therapeutic burp cloth recited in claim 8, wherein the closing mechanism is a first closing mechanism for sealing the fixed first pocket in a closed position, and a second closing mechanism for sealing the fixed second pocket in a closed position.

11. The therapeutic burp cloth recited in claim 8, wherein the at least one pad is at least one heating pad that is adapted to be secured in either the fixed first pocket or the fixed second pocket.

12. The therapeutic burp cloth recited in claim 8, wherein the at least one pad is at least one cold pad that is adapted to be secured in either the fixed first pocket or the fixed second pocket.

13. The therapeutic burp cloth recited in claim 8, further comprising at least one therapeutic insert for aromatherapy that is adapted to be secured in either the fixed first pocket or the fixed second pocket.

14. The therapeutic burp cloth recited in claim 13, further comprising an attachment mechanism for securing the therapeutic insert in the fixed pocket in the first pocket or the fixed second pocket.

15. A therapeutic burp cloth kit comprising:

a therapeutic burp cloth having a first elongated straight edge and a second elongated curved edge, the therapeutic burp cloth having:

at least one panel; and at least one fixed pocket, wherein an opening of the at least one fixed pocket is disposed within the second elongated curved edge of the at least one panel, wherein a closing mechanism is provided on the opening of the at least one fixed pocket to seal the fixed pocket in a closed position, and wherein at least one pad has a length sized slightly smaller than an opening length so that when the pad is inserted therein and the closing mechanism is in the closed position, the pad is unable to substantially move or exit from the pocket;

at least one heat pad;

at least one cold pad;

at least one therapeutic insert adapted for aromatherapy;

at least one dispenser to dispense aromatherapy mixtures onto the therapeutic insert and wherein the therapeutics burp cloth has a top panel, a middle panel and a bottom panel, wherein the at least one fixed pocket is disposed within the middle panel or the bottom panel.

16. The therapeutic burp cloth kit recited in claim 15, wherein the opening for the fixed pocket in the middle panel, or the opening for the fixed pocket in the bottom panel are disposed within the second elongated curved edge of the therapeutic burp cloth that is adapted to contour to a caregiver's body.

* * * * *